United States Patent
Yin

(10) Patent No.: US 11,904,316 B2
(45) Date of Patent: Feb. 20, 2024

(54) MICROFLUIDIC CHIP AND DETECTION METHOD THEREOF, MICRO TOTAL ANALYSIS SYSTEM

(71) Applicant: BOE TECHNOLOGY GROUP CO., LTD., Beijing (CN)

(72) Inventor: Yudan Yin, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 708 days.

(21) Appl. No.: 17/255,981

(22) PCT Filed: May 15, 2020

(86) PCT No.: PCT/CN2020/090493
§ 371 (c)(1),
(2) Date: Dec. 23, 2020

(87) PCT Pub. No.: WO2020/228816
PCT Pub. Date: Nov. 19, 2020

(65) Prior Publication Data
US 2021/0170407 A1   Jun. 10, 2021

(30) Foreign Application Priority Data

May 15, 2019   (CN) .......................... 201910403124.7

(51) Int. Cl.
*B01L 1/00*   (2006.01)
*B01L 3/00*   (2006.01)
(Continued)

(52) U.S. Cl.
CPC ......... *B01L 3/502715* (2013.01); *B01L 9/527* (2013.01); *G01N 33/54346* (2013.01); *B01L 2200/10* (2013.01); *B01L 2300/161* (2013.01)

(58) Field of Classification Search
None
See application file for complete search history.

(56) References Cited

U.S. PATENT DOCUMENTS

| 9,810,623 B2 | 11/2017 | Ghaffari et al. |
| 2006/0226030 A1 | 10/2006 | Hanke et al. |

(Continued)

FOREIGN PATENT DOCUMENTS

| CN | 101738357 A | 6/2010 |
| CN | 102265144 A | 11/2011 |

(Continued)

OTHER PUBLICATIONS

China Patent Office, First Office Action dated Dec. 23, 2020, for corresponding Chinese application 201910403124.7.

*Primary Examiner* — Jyoti Nagpaul
(74) *Attorney, Agent, or Firm* — HOUTTEMAN LAW LLC

(57) ABSTRACT

The present disclosure provides a microfluidic chip, including: a support and an NFC coil in the support, and a flow path is provided in the support and is isolated from the NFC coil; the flow path includes at least one detection window region with a stationary phase therein, and the stationary phase is used to specifically capture a target analyte, the detection window region at least partially overlaps with the NFC coil in a thickness direction of the support. The present disclosure further provides a detection method of the microfluidic chip and a micro total analysis system. The present disclosure can quickly and immediately obtain a detection result.

20 Claims, 2 Drawing Sheets

(51) Int. Cl.
*B01L 9/00* (2006.01)
*G01N 33/543* (2006.01)

(56) References Cited

U.S. PATENT DOCUMENTS

| | | |
|---|---|---|
| 2010/0123457 A1 | 5/2010 | Shinoda |
| 2017/0020424 A1 | 1/2017 | Holweg et al. |
| 2017/0259267 A1 | 9/2017 | Kim et al. |
| 2020/0378886 A1* | 12/2020 | Chou ................ G01N 21/0303 |

FOREIGN PATENT DOCUMENTS

| | | |
|---|---|---|
| CN | 104965080 A | 10/2015 |
| CN | 105044329 A | 11/2015 |
| CN | 106062544 A | 10/2016 |
| CN | 107049604 A | 8/2017 |
| CN | 108212228 A | 6/2018 |
| CN | 207851078 U | 9/2018 |
| CN | 108663525 A | 10/2018 |
| CN | 109174219 A | 1/2019 |
| CN | 109499634 A | 3/2019 |
| CN | 110090675 A | 8/2019 |
| EP | 2924441 A | 9/2015 |
| WO | WO2005001479 A | 1/2005 |

* cited by examiner

A-A

MICROFLUIDIC CHIP AND DETECTION METHOD THEREOF, MICRO TOTAL ANALYSIS SYSTEM

CROSS REFERENCE TO RELATED APPLICATIONS

The present application claims the priority of the Chinese Patent Application No. 201910403124.7 filed on May 15, 2019, the content of which is incorporated herein by reference in its entirety.

TECHNICAL FIELD

The present disclosure relates to the technical field of immunodetection, in particular to a microfluidic chip and a detection method thereof, and a micro total analysis system.

BACKGROUND

Microfluidic chip technology is a technology that a plurality of units for basic operations such as preparation, transportation, reaction, separation, detection for biological or chemical sample are integrated on one chip, and has been rapidly developed in the fields of medicine, chemistry, material science, life science and the like due to its unique advantages such as little biological sample consumption, high analysis speed, low cost, easy miniaturization, integration, portability and the like.

SUMMARY

The present disclosure provides a microfluidic chip and a detection method thereof, and a micro total analysis system.

The present disclosure provides a microfluidic chip, including: a support, an near field communication (NFC) coil and a flow path in the support, and the flow path is isolated from the NFC coil; the flow path includes at least one detection window region with a stationary phase therein, and the detection window region at least partially overlaps with the NFC coil in a thickness direction of the support, to change a value of at least one radiation parameter of the NFC coil when the stationary phase specifically captures a target analyte.

In some implementations, the flow path includes a plurality of detection window regions, different detection window regions have different stationary phases therein; and when materials with a same dielectric constant are filled in any two detection window regions at different times, radiation parameters of the NFC coil are different.

In some implementations, a portion of the NFC coil that overlaps with each detection window region is a single line segment, and lengths of line segments corresponding to different detection window regions are different.

In some implementations, the flow path includes a plurality of detection window regions, different detection window regions have different stationary phases therein; and when materials with a same dielectric constant are filled in any two detection window regions at different times, radiation parameters of the NFC coil are the same.

In some implementations, the support includes: a substrate, an insulating layer on the substrate and a cover on the insulating layer, where a groove is provided in the insulating layer at a side proximal to the cover, and the cover and the groove enclose the flow path.

In some implementations, the support includes: a substrate, an insulating layer on the substrate and a cover on the insulating layer, where a groove is provided in the cover at a side proximal to the insulating layer, and the groove and the insulating layer enclose the flow path.

In some implementations, the NFC coil is a planar metal coil wound on the substrate, and the insulating layer covers the NFC coil to isolate the NFC coil from the flow path; and the NFC coil includes a plurality of first wires extending along a first direction and a plurality of second wires extending along a second direction, wherein the first direction and the second direction intersect with each other.

In some implementations, a distance between the flow path and the NFC coil is not greater than 300 nm.

In some implementations, the flow path includes a plurality of detection window regions, and the plurality of detection window regions are respectively overlapped with a plurality of portions with different lengths of a same one of the first wires or a same one of the second wires.

In some implementations, the flow path includes a plurality of detection window regions, and the plurality of detection window regions are respectively overlapped with a plurality of portions with a same length of a same one of the first wires or a same one of the second wires, and distances between the plurality of detection window regions and a center of the NFC coil are different.

In some implementations, a width of the flow path is in a range of 20 μm to 400 μm.

In some implementations, the insulating layer is made of photoresist, and the substrate and the cover are made of glass.

In some implementations, a hydrophilic layer is provided on an inner wall of the flow path, and the hydrophilic layer may be a silicon dioxide layer.

In some implementations, a hydrogel is provided in the detection window region, and the stationary phase is pre-modified in the hydrogel.

In some implementations, the hydrogel includes a deoxyribonucleic acid (DNA) hydrogel or a polyethylene glycol (PEG) hydrogel.

Accordingly, the present disclosure further provides a micro total analysis system, including: the above microfluidic chip and an NFC reading device configured to obtain a magnitude of the radiation parameter of the NFC coil in the microfluidic chip.

Accordingly, the present disclosure further provides a detection method of the above microfluidic chip, including steps of:

driving liquid to be detected to flow along the flow path of the microfluidic chip;

obtaining the magnitude of the at least one radiation parameter of the NFC coil;

determining a detection result according to the magnitude of the at least one radiation parameter; where the detection result includes: whether various objects to be detected in the liquid to be detected contain the target analyte capable of being specifically captured by the stationary phases, and the target analyte is marked with modifiers capable of changing the at least one radiation parameter of the NFC coil.

In some implementations, the step of determining the detection result according to the magnitude of the radiation parameter includes:

determining the detection result corresponding to the obtained magnitude of the radiation parameter according to a preset mapping relationship, where the mapping relationship includes a corresponding relationship between a plurality of value ranges of the radiation parameter and respective corresponding detection results.

In some implementations, the modifier includes any one of nano-gold, nano-ferroferric tetrachloride and nano-ceramic.

BRIEF DESCRIPTION OF DRAWINGS

The accompanying drawings are used to provide a further understanding of the present disclosure and constitute a part of the specification, and are used to interpret the present disclosure together with the following specific embodiments, but do not constitute a limitation to the present disclosure. In the drawings.

DETAIL DESCRIPTION OF EMBODIMENTS

The specific embodiments of the present disclosure will be described in detail below with reference to the accompanying drawings. It should be understood that the specific embodiments described herein are merely used to illustrate and explain the present disclosure, and are not used to limit the present disclosure.

When the microfluidic chip in the related art detects a sample, it needs devices such as a scanner, a color development processing device to output a detection result, and thus the time for detecting the sample is prolonged.

Figure 1:
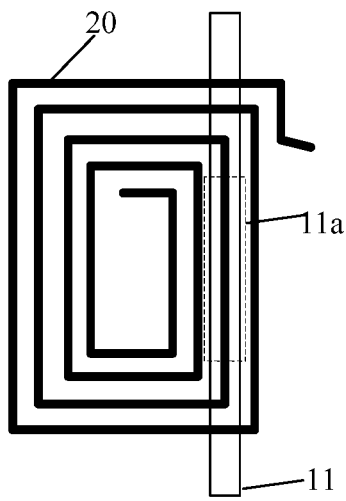
FIG. 1 is a top view of a microfluidic chip according to an embodiment of the present disclosure.
Figure 2:
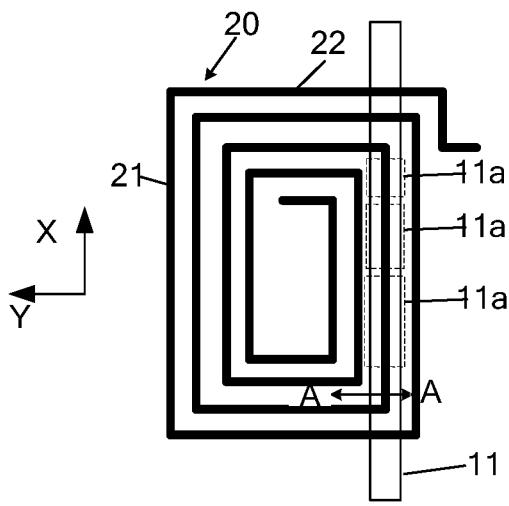
FIG. 2 is a top view of a microfluidic chip according to an embodiment of the present disclosure.
Figure 3:
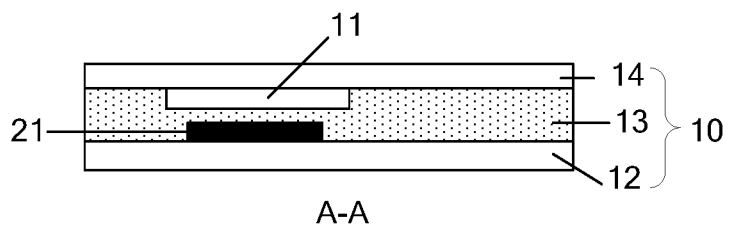
FIG. 3 is a cross-sectional view taken along AA line of FIG. 2.

FIG. 1 is a top view of a microfluidic chip according to an embodiment of the present disclosure, FIG. 2 is a top view of a microfluidic chip according to an embodiment of the present disclosure, and FIG. 3 is a cross-sectional view taken along AA line in FIG. 2. As shown in FIGS. 1 to 3, the microfluidic chip includes: a support 10 and an NFC (Near Field Communication) coil 20 provided in the support 10. A flow path 11 is provided in the support 10, and is isolated from the NFC coil 20, for example by an insulating layer 13 as shown in FIG. 3. The layer for the isolation is as thin as possible, for example, the thickness of the layer for the isolation is not greater than 300 nm. The flow path 11 includes at least one detection window region 11a in which a stationary phase is provided, and the stationary phase is used for specifically capturing a target analyte, and each detection window region 11a at least partially overlaps with one trace of the NFC coil 20 in a thickness direction of the support 10. That is, the present disclosure applies the near field communication technology to the microfluidic chip, and detects a biological sample by using a non-contact identification technology of the near field communication.

As shown in FIG. 3, the flow path 11 covers only one trace of the NFC coil 20 in a width direction to avoid affecting traces in other areas. A width of the flow path 11 is typically set between 20 μm and 400 μm based on a trace width of the NFC coil 20.

The stationary phase may be an antigen/antibody. The microfluidic chip may be used in immunodetection, and particularly is used for detecting whether a liquid contains a target analyte, where the target analyte is an antibody/antigen capable of specifically binding to the stationary phase. For example, if the stationary phase is a hepatitis B antibody, the target analyte is a hepatitis B antigen capable of specifically binding to the hepatitis B antibody. The target analyte is captured by specific interaction with the stationary phase.

The NFC coil 20 is a coil in near field communication, and the coil is a planar metal coil formed by winding layer by layer and from inside to outside (or from outside to inside), and may be wound into a rectangular shape, a circular shape, or other shapes. As shown in FIGS. 1 to 3, the metal coil 20 may be wound on a substrate 12, and two ends of the coil are connected to an NFC peripheral chip, for performing the near field communication in cooperation with an NFC reading device. When the NFC coil 20 approaches the NFC reading device, the NFC reading device sends an electromagnetic wave signal to the NFC coil 20, and determines a magnitude of a radiation parameter (e.g., a center frequency, a port parameter, a resonance frequency, etc.) of the NFC coil 20 according to the electromagnetic wave signal reflected by the NFC coil 20.

When the microfluidic chip of the present embodiment is used for immunodetection, a modifier (for example, nano-gold, nano-ceramic, etc.) may be marked on various objects to be detected in the liquid to be detected. In this way, after the stationary phase in the detection window region captures the target analyte, due to the presence of the modifier, an electromagnetic property (mainly, dielectric constant) of the detection window region may be changed, and thus the magnitude of the radiation parameter of the NFC coil 20 is changed. At this time, as long as the radiation parameter of the NFC coil 20 is read by the NFC reading device, it may be quickly determined whether the stationary phase has captured the target analyte, that is, whether the target analyte capable of being captured by the stationary phase exists in the liquid to be detected. Therefore, the microfluidic chip in the embodiment may obtain the detection result conveniently and instantly by using the near field communication technology.

As shown in FIG. 3, the support 10 includes: the substrate 12, the insulating layer 13 and a cover 14 provided on the substrate 12, where the cover 14 is provided on a side of the insulating layer 13 distal to the substrate 12, a groove is provided in the insulating layer 13, and the flow path 11 is surrounded (enclosed) by the cover 14 and the groove. A hydrophilic layer is provided on an inner wall of the flow path 11.

Both the substrate 12 and the cover 14 may be glass substrates, and the insulating layer 13 may be made of photoresist. The groove is formed by exposing and developing the photoresist. The hydrophilic layer may be specifically a modified layer of a $SiO_2$ layer, which may be formed by sputtering. Certainly, the groove forming the flow path 11 may be formed in a surface of the cover 14 proximal to the substrate 12.

Figure 4:
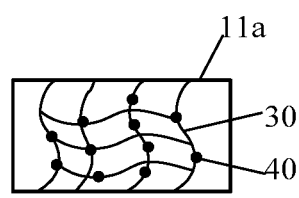
FIG. 4 is a schematic cross-sectional view of a detection window region.

FIG. 4 is a schematic cross-sectional view of a detection window region of the flow path 11. As shown in FIG. 4, the detection window region 11a is provided with a hydrogel 30, and the stationary phase 40 is previously modified in the hydrogel 30. By providing the hydrogel 30, more stationary phases 40 may be modified in the detection window region, thereby capturing more target analytes and further improving the detection accuracy.

The hydrogel 30 includes a DNA hydrogel or a PEG hydrogel.

As shown in FIG. 1, there is one detection window region 11a; alternatively, as shown in FIG. 2, there are a plurality of detection window regions 11a. In the case that the number of the detection window region 11a is one, when the liquid to be detected contains the target analyte corresponding to the stationary phase, and the target analyte is captured, the magnitude of the radiation parameter of the NFC coil 20 changes. At this time, it is determined that the liquid to be detected contains the target analyte corresponding to the stationary phase according to the change of the magnitude of the radiation parameter.

In the case where the flow path 11 includes the plurality of detection window regions 11a, different stationary phases are provided in different detection window regions 11a. It will be appreciated that each stationary phase specifically captures the respective target analyte, i.e., different stationary phases are used to capture different target analytes, thereby allowing for identification of the different target analytes.

It should be noted that a type of material in the detection window region 11a, physical parameters of the detection window region 11a (for example, a length of a wire of the NFC coil 20 in the detection window region 11a, a distance from the detection window region 11a to a center of the NFC coil 20, etc.) all affect a value of the radiation parameter of the NFC coil 20. Therefore, in order to determine whether all the objects to be detected in the liquid to be detected include the target analyte corresponding to the stationary phase 40 in each detection window region 11a, when the physical parameters of the detection window regions 11a are the same, modifiers for marking different objects to be detected are different; when the physical parameters of the detection window regions are different, modifiers for marking different objects to be detected may be the same or different; thereby ensuring that values of the radiation parameter of the NFC coil 20 are different when different detection window regions 11a capture the target analyte by saturation at different times respectively.

In some implementations, the plurality of detection window regions 11a are provided in a manner such that: when materials having a same dielectric constant are filled (captured) in any two detection window regions 11a at different times, radiation parameters of the NFC coil 20 are different. That is, physical parameters of the plurality of detection window regions 11a are different.

Specifically, as shown in FIG. 2, a portion of the NFC coil 20 overlapping each detection window region 11a is a single line segment, and lengths of line segments corresponding to different detection window regions 11a are different. Further, the NFC coil 20 includes a plurality of first wires 21 extending in a first direction X and a plurality of second wires 22 extending in a second direction Y, and the first direction and the second direction intersect with each other; the plurality of detection window regions 11a overlap different portions of a same one of the first wires 21, resulting in overlapping regions have different lengths.

Certainly, the lengths of the line segments corresponding to different detection window regions 11a may be the same, and distances from the different detection window regions 11a to the center of the NFC coil 20 may be different.

In other implementations, the plurality of detection window regions 11a are provided in a manner such that: when the materials having a same dielectric constant are filled (captured) in any two detection window regions 11a at different times, the radiation parameters of the NFC coil 20 are the same. That is, the physical parameters of the plurality of detection window regions 11a are the same.

Specifically, the portion of the NFC coil 20 that overlaps with each detection window region 11a is a single line segment, and the lengths of the line segments corresponding to different detection window regions 11a are different. However, the present disclosure is not limited thereto. The line segment of the NFC coil 20 corresponding to each detection window region 11a may be a plurality of discontinuous line segments, and may even include corners of the trace of the NFC coil 20. Such an arrangement including the corners of the trace may lose a linearity of some data, which may be overcome by knowing the length of the line segment corresponding to measured values of each detection window region 11a. However, in consideration of the filling of the hydrogel 30 in the flow path 11, the trace corresponding to each detection window region 11a is typically provided as a single line segment.

Figure 5:
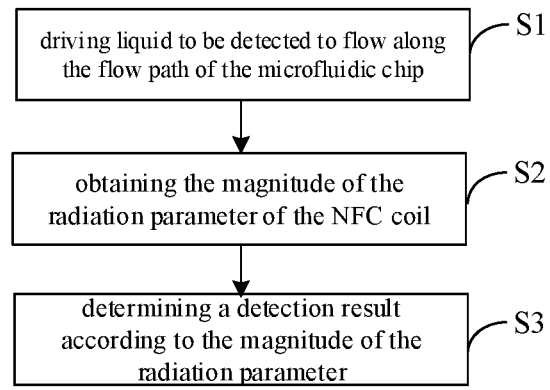
FIG. 5 is a flow chart of a detection method of a microfluidic chip according to the present disclosure.

FIG. 5 is a flowchart of a detection method of the microfluidic chip provided by the present disclosure, and as shown in FIG. 5, the detection method includes following steps S1 to S3.

S1, driving the liquid to be detected to flow along the flow path of the microfluidic chip, where the liquid to be detected contains at least one object to be detected marked with the modifier.

The method for driving the liquid to be detected is not particularly limited in the present disclosure, and for example, the liquid is driven to flow by a mechanical driving or an electrophoresis/electroosmosis manner.

The object to be detected is marked with the modifier for changing the dielectric constant of a medium in the flow path when the object to be detected is captured. The modifier includes any one of nano-gold, nano-ferroferric tetrachloride and nano-ceramic.

Figure 6:
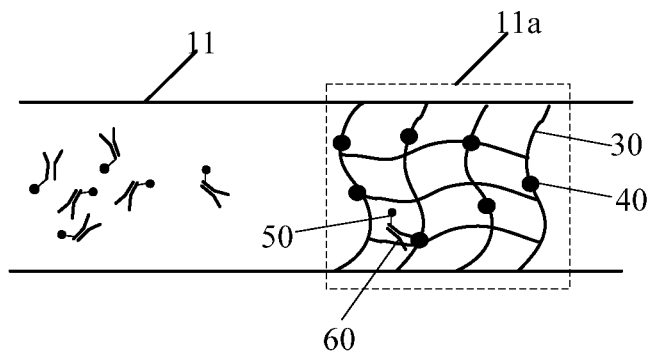
FIG. 6 is a schematic view of a target analyte captured by the detection window region.

FIG. 6 is a schematic view of the target analyte captured by the detection window region. As shown in FIG. 6, when the liquid to be detected flows along the flow path, the stationary phase 40 in the detection window region 11a is specifically bonded to the corresponding target analyte 60, so that the target analyte 60 is captured, and the rest of objects to be detected continue to flow forward without being captured. Since the target analyte 60 is marked with the modifier 50, when the target analyte 60 is captured by the detection window region 11a, the dielectric constant of the detection window region 11a changes, so that the magnitude of the radiation parameter of the NFC coil changes.

S2, obtaining the magnitude of the radiation parameter of the NFC coil.

As described above, the radiation parameter may be a center frequency, a port parameter, a resonance frequency, and the like. The magnitude of the radiation parameter may be obtained by using the NFC reading device.

S3, determining a detection result according to the magnitude of the radiation parameter; the detection result includes: whether or not the objects to be detected in the liquid to be detected contain the target analyte capable of being specifically captured by the stationary phase.

The step S3 specifically includes: determining the detection result corresponding to the obtained magnitude of the radiation parameter according to a preset mapping relationship, where the mapping relationship includes a corresponding relationship between a plurality of value ranges of the radiation parameter and respective corresponding detection results. The mapping relationship may be obtained in advance through an experimental manner.

For example, when the flow path includes one detection window region, as shown in FIG. 1, a stationary phase A is provided in the detection window region. In this case, a modifier X is marked on a target analyte A1 capable of specifically binding to the stationary phase A, and a liquid sample including the target analyte A1 is introduced into the flow path, so that the target analyte A1 marked with the modifier X is captured by saturation in the detection window region. At this time, the value of the radiation parameter of the NFC coil is detected, and a first value range fluctuating around the value is determined; values in the first value range correspond to the detection result of "the liquid to be detected contains the target analyte A1"; the other values outside the first value range correspond to the detection result of "the liquid to be detected does not contain the target analyte A1". When the microfluidic chip is used for immunodetection, the modifier X is marked in the object to be detected of the liquid to be detected, the liquid to be detected is driven to flow along the flow path. If it is detected that the value of the radiation parameter of the NFC coil is in the first value range, it is determined that the liquid to be detected contains the target analyte A1, and if it is detected that the value of the radiation parameter of the NFC coil is not in the first value range, it is determined that the liquid to be detected does not contain the target analyte A1.

For example, when the flow path includes three detection window regions, as shown in FIG. 2, the three detection window regions are respectively provided with a stationary phase A, a stationary phase B, and a stationary phase C; a portion of the NFC coil 20 overlapping each detection window region is a single line segment, and the lengths of the line segments corresponding to different detection window regions are different. In this case, modifiers X are marked on a target analyte A1 capable of specifically binding to the stationary phase A, on a target analyte B1 capable of specifically binding to the stationary phase B, and on a target analyte C1 capable of specifically binding to the stationary phase C; then, a plurality of liquid samples (for example, the target analytes contained in the plurality of liquid samples are respectively: A1, B1, C1, A1+B1, A1+C1, B1+C1, and A1+B1+C1) containing incompletely same types of target analytes are introduced into the flow path, respectively, the value of the radiation parameter corresponding to each liquid sample is detected, and the value range of the radiation parameter corresponding to each liquid sample is determined. When the microfluidic chip is used for immunodetection, the modifier X is marked on each object to be detected in the liquid to be detected, the liquid to be detected is driven to flow along the flow path, and the type of the target analyte in the liquid to be detected is determined according to the value of the radiation parameter of the NFC coil and the value range of the radiation parameter corresponding to each liquid sample.

As described above, the plurality of detection window regions may be provided according to the following conditions: when materials with a same dielectric constant are captured in any two detection window regions at different times, the radiation parameters of the NFC coil are the same. In this case, the modifiers marked on different types of objects to be detected in the liquid to be detected are different, so that the radiation parameters of the NFC coil are different when the types of the target analytes in the liquid to be detected are different.

For example, when the flow path includes two detection window regions, the two detection window regions are respectively provided with a stationary phase A and a stationary phase B, the stationary phase A may specifically bind to a target analyte A1, and a modifier A2 is marked on the target analyte A1; the stationary phase B may specifically bind to a target analyte B1, and a modifier B2 is marked on the target analyte B1; the portion of the NFC coil 20 overlapping each detection window region is a single line segment, and the lengths of the line segments corresponding to different detection window regions are the same. In this case, before performing the detection, the modifier A2 is marked on the target analyte A1 and the modifier B2 is marked on the target analyte B1; then, a first liquid sample containing the target analyte A1, a second liquid sample containing the target analyte B1, and a third liquid sample containing the target analytes A1+B1 are respectively introduced into the flow path, and a value of the radiation parameter corresponding to each liquid sample is detected, so that a value range of the radiation parameter corresponding to each liquid sample is determined. When the microfluidic chip is used for immunodetection, the modifier A2, the modifier B2, the modifier A2+the modifier B2 are respectively marked in the liquid to be detected; and whether the liquid to be detected contains the target analyte A1/the target analyte B1 or not is determined according to values of the radiation parameter corresponding to the liquid to be detected marked with the three modifiers and value ranges of the radiation parameter corresponding to the three liquid samples.

Figure 7:
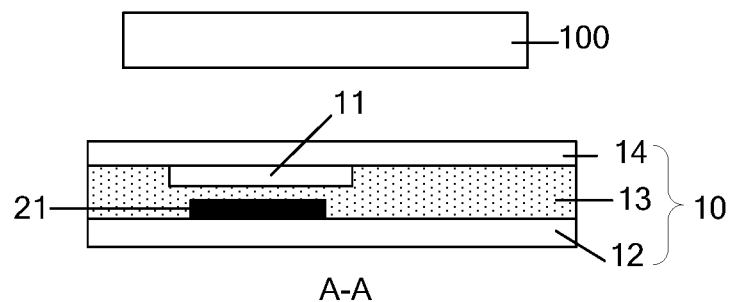
FIG. 7 is a schematic diagram of a micro total analysis system according to the present disclosure.

The present disclosure further provides a micro total analysis system, as shown in FIG. 7, which includes an NFC reading device 100 and the above microfluidic chip, where the NFC reading device 100 is configured to obtain a magnitude of a radiation parameter of an NFC coil in the microfluidic chip.

Specifically, the NFC reading device is used for sending an electromagnetic wave signal to the NFC coil when the NFC reading device is relatively near the microfluidic chip, and the magnitude of the radiation parameter of the NFC coil is determined according to the electromagnetic wave signal reflected by the NFC coil.

The NFC reading device 100 may be a smart device such as a mobile phone or a reader having an NFC response module.

It will be understood that the above embodiments are merely exemplary embodiments employed to illustrate principles of the present disclosure, and the present disclosure is not limited thereto. It will be apparent to those skilled in the art that various changes and modifications may be made therein without departing from the spirit and scope of the present disclosure, and these changes and modifications are to be considered within the scope of the present disclosure.

What is claimed is:

1. A microfluidic chip, comprising: a support, and an NFC coil and a flow path in the support, wherein
   the flow path is isolated from the NFC coil;
   the flow path comprises at least one detection window region each with a stationary phase therein, and
   the detection window region at least partially overlaps with the NFC coil in a thickness direction of the support, to change a value of at least one radiation parameter of the NFC coil when the stationary phase specifically captures a target analyte.

2. The microfluidic chip according to claim 1, wherein the flow path comprises a plurality of detection window regions, and different detection window regions have different stationary phases therein; and
   when materials with a same dielectric constant are filled in any two detection window regions at different times, values of the at least one radiation parameter of the NFC coil are different.

3. The microfluidic chip according to claim 2, wherein a portion of the NFC coil that overlaps with each detection window region is a single line segment, and lengths of line segments corresponding to different detection window regions are different.

4. The microfluidic chip according to claim 1, wherein the flow path comprises a plurality of detection window regions, and different detection window regions have different stationary phases therein; and
when materials with a same dielectric constant are filled in any two detection window regions at different times, values of the at least one radiation parameter of the NFC coil are the same.

5. The microfluidic chip according to claim 1, wherein the support comprises a substrate, an insulating layer on the substrate and a cover on the insulating layer, and
a groove is provided in the insulating layer at a side proximal to the cover, and the cover and the groove enclose the flow path.

6. The microfluidic chip according to claim 5, wherein the NFC coil is a planar metal coil wound on the substrate, and the insulating layer covers the NFC coil to isolate the NFC coil from the flow path; and
the NFC coil comprises a plurality of first wires extending along a first direction and a plurality of second wires extending along a second direction, wherein the first direction and the second direction intersect with each other.

7. The microfluidic chip according to claim 6, wherein a distance between the flow path and the NFC coil is not greater than 300 nm.

8. The microfluidic chip according to claim 6, wherein the flow path comprises a plurality of detection window regions, and
the plurality of detection window regions overlap with a plurality of portions with different lengths of a same one of the first wires or a same one of the second wires, respectively.

9. The microfluidic chip according to claim 8, wherein a width of the flow path is in a range of 20 µm to 400 µm.

10. The microfluidic chip according to claim 6, wherein the flow path comprises a plurality of detection window regions, and
the plurality of detection window regions are overlapped with a plurality of portions with a same length of a same one of the first wires or a same one of the second wires, respectively, and distances between the plurality of detection window regions and a center of the NFC coil are different.

11. The microfluidic chip according to claim 5, wherein the insulating layer is made of photoresist, and the substrate and the cover are made of glass.

12. The microfluidic chip according to claim 1, wherein the support comprises a substrate, an insulating layer on the substrate and a cover on the insulating layer, an
a groove is provided in the cover on a side proximal to the insulating layer, and the groove and the insulating layer enclose the flow path.

13. The microfluidic chip according to claim 1, wherein a hydrophilic layer is provided on an inner wall of the flow path.

14. The microfluidic chip according to claim 13, wherein the hydrophilic layer is a silicon dioxide layer.

15. The microfluidic chip according to claim 1, wherein a hydrogel is provided in the detection window region, and the stationary phase is pre-modified in the hydrogel.

16. The microfluidic chip according to claim 15, wherein the hydrogel comprises a DNA hydrogel or a PEG hydrogel.

17. A micro total analysis system, comprising: the microfluidic chip of claim 1 and an NFC reading device configured to obtain a magnitude of the at least one radiation parameter of the NFC coil in the microfluidic chip.

18. A detection method of the microfluidic chip according to claim 1, comprising:
driving liquid to be detected to flow along the flow path of the microfluidic chip;
obtaining a magnitude of the at least one radiation parameter of the NFC coil;
determining a detection result according to the magnitude of the at least one radiation parameter; wherein the detection result comprises: whether various objects to be detected in the liquid to be detected contain the target analyte capable of being specifically captured by the stationary phase, wherein the target analyte is marked with modifiers capable of changing the magnitude of the at least one radiation parameter of the NFC coil.

19. The detection method according to claim 18, wherein the determining the detection result according to the magnitude of the at least one radiation parameter comprises:
determining the detection result corresponding to the obtained magnitude of the at least one radiation parameter according to a preset mapping relationship, wherein the preset mapping relationship comprises correspondence between a plurality of values of the at least one radiation parameter and respective detection results.

20. The detection method according to claim 18, wherein the modifier comprises any one of nano-gold, nano-ferroferric tetrachloride and nano-ceramic.

* * * * *